United States Patent [19]

Ohsawa et al.

[11] 4,404,859
[45] Sep. 20, 1983

[54] FLOWMETER

[75] Inventors: Katsuyuki Ohsawa, Nagoya; Katsuhiko Sugiyama, Aichi; Yoshinori Idota, Nagoya, all of Japan

[73] Assignee: Kabushiki Kaisha Toyota Chuo Kenkyusho, Aichi, Japan

[21] Appl. No.: 341,112

[22] Filed: Jan. 20, 1982

[30] Foreign Application Priority Data

Jan. 26, 1981 [JP] Japan ................................ 56-9888

[51] Int. Cl.³ .............................................. G01F 1/20
[52] U.S. Cl. ............................. 73/861.18; 73/861.19; 73/861.21
[58] Field of Search ........... 73/861.18, 861.19, 861.63, 73/DIG. 8, 118, 861.21; 137/808, 803; 235/201 PF

[56] References Cited

U.S. PATENT DOCUMENTS 3,714,828 2/1973 Durkan ........................ 73/DIG. 8

*Primary Examiner*—Charles A. Ruehl

*Attorney, Agent, or Firm*—Oblon, Fisher, Spivak, McClelland & Maier

[57] ABSTRACT

A flowmeter comprises a first tube having a first flow passage therethrough with its cross-sectional area being smaller at the outlet than at the inlet, a second tube disposed substantially concentrically within the first flow passage and having a second flow passage therethrough with its cross-sectional area being minimum substantially midway thereof, a third flow passage providing fluid communication between ports opening respectively at a sidewall of the second tube into the second flow passage adjacent to the minimum portion and at a sidewall of the first tube into the first flow passage, and a sensor disposed in either the third flow passage, the sidewall of the first tube, or the sidewall of the second tube for detecting periodic variations of a fluid flowing through the first, second, or third flow passage. The flowmeter detects the frequency of variations in the pressure or speed of a fluid, thus detecting the rate of flow of the fluid through the first and second tubes.

9 Claims, 5 Drawing Figures

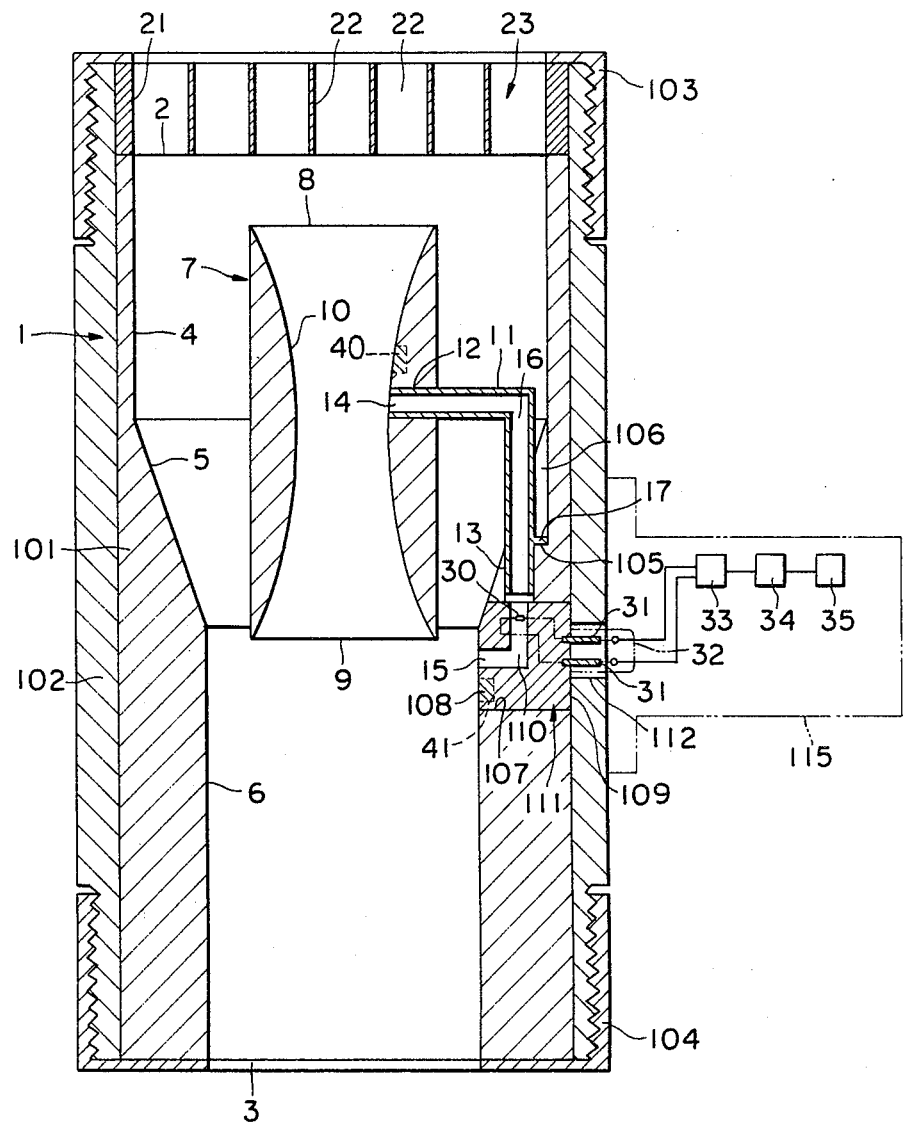

FLOWMETER

BACKGROUND OF THE INVENTION

1. Field of the Invention

The present invention relates to a flowmeter for measuring the rate of flow of a fluid through a passage on the basis of vibrations of the fluid as it flows through the passage.

2. Description of the Prior Art

Various flowmeters are known for indirectly measuring the rate of flow of a fluid by determining its speed of flow by way of measurement of the frequency of vibrations of the fluid which are caused within a passage of the meter, the vibrations being substantially proportional to the speed of flow of the fluid through the passage. Flowmeters of this kind include Kármán vortex flowmeter, fluidic flowmeters, and rotational air flow meters.

These flowmeters are subjected to less measuring errors than other types of flowmeter such as orifice flowmeters and hot-wire flowmeters. More specifically, the orifice flowmeter includes a pressure sensor for detecting the pressure of a fluid at a throat. Since the output of the pressure sensor is a quadratic function of the rate of flow of the fluid, the orifice flowmeter suffers from large detecting errors in the range of low rates of fluid flow. The hot-wire flowmeter utilizes a hot wire for direct measurement of the speed of flow of a fluid. Attempts to improve responsiveness of the flow meter require that the hot wire sensor be thin and small in size. Such arrangement however results in poor durability. The hot-wire flowmeter is also disadvantageous in that it needs a linearization device for electric arithmetic operations which lead to a complex computation and display processing.

Flowmeters which operate on the basis of fluid vibations are only required to detect the period of such vibrations for measuring either pressures or speeds of flow. No high precision for the output of a sensor is necessary for flowmeters in this category, and since the measured period of vibrations is in linear relation to the speed or the rate of flow of the fluid, arithmetic operations required to derive the rate of flow are quite simple and flowmeter apparatus are inexpensive to construct.

The Kármán vortex flowmeter includes a blunt-headed body disposed in a flow passage for producing Karman vortices behind the blunt-headed body, and the frequency of generations of Kármán vortices is measured to find the rate of flow. For stable formation of Kármán vortices, the shape and structure of the blunt-headed body are designed or selected to suit the fluid passage and the fluid to be measured. In some applications, the blunt-headed body has a fluid passage therethrough, or the positional relationship between the blunt-headed body and the wall of the flow passage is optimized. Although the above structural designs are easily comprehensible from the theoretical standpoint, various difficulties are encountered to provide actual arrangements to form Kármán vortices stably.

The fluidic flowmeter is characterized in that symmetrical feedback loop openings are defined in sidewalls of a flow passage for a main fluid to inject control fluid flows from the feedback loops into the main fluid for periodically attaching the latter alternately to the sidewalls. The rate of flow of the main fluid can be determined by detecting the period of such periodic oscillation of the main fluid. Although fluid vibrations are relatively stable, control fluid flows injected from the feedback loops into the main fluid are required to have a sufficient controlling effect on the main flow in order to oscillate the main fluid flow stably into alternate attachment to the sidewalls. The fluidic flowmeter is therefore suitable for use with main fluid passages having a relatively small diameter, but is not applicable to fluid passages of a relatively large diameter handling a large amount of fluid.

The rotational air flow meter has a guide in an inlet of the meter for generating a swirling fluid flow within a venturi. The guide however also serves to give resistance to the flow of a fluid, and results in a complicated structure.

SUMMARY OF THE INVENTION

It is an object of the present invention to provide a flowmeter operable on the basis of vibrations of fluid being measured, which flowmeter is simple in construction and capable of generating and sustaining fluid vibrations stably.

Another object of the present invention is to provide a flowmeter which is suitable for measurement of both small and large rates of fluid flow and will cause a less pressure loss.

Still another object of the present invention is to provide a flowmeter which is small in size and lightweight for detecting and displaying the frequency of vibrations of a fluid being measured.

Still another object of the present invention is to provide a flowmeter optimum for measuring the rate of flow of air through an intake supply device in an automotive engine.

The flowmeter according to the present invention is of a double venturi structure, in which a throat portion of an inner venturi and that of an outer venturi (the latter throat being located adjacent to an output of the inner venturi) are connected through a feedback loop. The inner venturi has a divergent portion located downstream of its throat portion and shaped so that the fluid flow therethrough may be separated from the sidewall of the inner venturi to form vortices either considerably or slightly in an unstable manner.

This structure allows a feedback flow to be produced through the feedback loop to the throat portion of the inner venturi due to the difference between the pressures at the throat portions of the inner and outer venturies, with the result that the separated flow (including vortices) is increased due to such feedback flow. As a result, the difference between the pressures at the throat portions of the inner and outer venturies comes to be eliminated to stop the feedback flow, which leads to the decrease of the separated flow. Then, the pressure difference is again produced. Thus, the change in the pattern or condition of the fluid flow periodically occurs. With the increase in the flow rate or flow speed, the period at which the pattern of the fluid flow changes becomes short.

The present invention utilizes the principle that the periodic variation in the flow speed or fluid pressure resulted from the change in the pattern of the fluid flow is proportional to the flow rate. Namely, the flowmeter of the invention detects rate of the flow therethrough by detecting such periodic variation.

This flowmeter thus possesses advantages of both the Kármán vortex flowmeter and the fluidic flowmeter.

According to the present invention, a flowmeter comprises a first tube having an inlet and an outlet at axial ends thereof and a first flow passage having a cross-sectional area extending perpendicularly to a central axis of the first tube and smaller at said outlet than at the inlet, the first tube having a first port defined in a sidewall thereof and opening into the first flow passage, and a second tube disposed substantially concentrically within the first flow passage of the first tube and having an inlet and an outlet at axial ends thereof and a second flow passage having a cross-sectional area which is minimum substantially midway of the second tube in an axial direction thereof, the second tube having a second port defined in a side-wall thereof and opening into the second flow passage at the minimum cross-sectional area thereof. The second tube is supported within the first tube by a support pipe which defines therethrough a third flow passage providing fluid communication between said first and second ports. A sensor is disposed in either the third flow passage, the sidewall of the first tube, or the sidewall of the second tube for detecting periodic variations in the condition of a fluid flowing through the first, second, or third flow passage.

The above and other objects, features and advantages of the present invention will become more apparent from the following description when taken in conjunction with the accompanying drawings in which certain preferred embodiments of the invention are shown by way of illustrative example.

BRIEF DESCRIPTION OF THE DRAWINGS

FIG. 3 is a cross-sectional view of a flowmeter according to an embodiment of the present invention;

DETAILED DESCRIPTION

Figure 2:
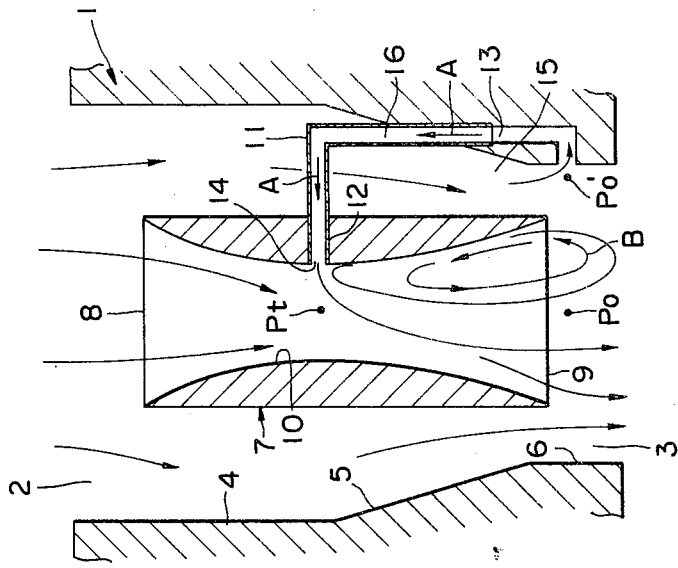
FIGS. 1 and 2 are schematic cross-sectional views illustrative of the principles on which a flowmeter of the present invention operates.
Figure 1:
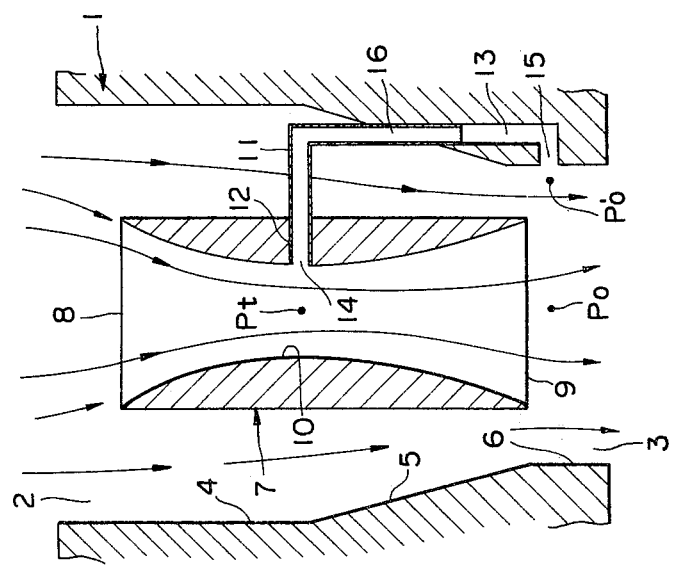

In FIGS. 1 and 2 which show the principles of a flowmeter of the present invention, a first tube 1 includes inlet and outlet ends 2, 3 which are interconnected by a flow passage defined jointly by a first cylindrical surface 4, a conical taper surface 5 in the form of a truncated cone, and a second cylindrical surface 6 having a smaller diameter than that of the first cylindrical surface 4, the surfaces 4, 5 and 6 being concentrically connected in the order named. A second tube 7 is concentrically disposed in the first tube 1 and has inlet and outlet ends 8, 9 interconnected by a flow passage defined by an arcuate sidewall 10 lying in a plane containing a central axis of the second tube 7. The flow passage in the second tube 7 has a minimum cross-sectional area extending transversely of the central axis of the second tube 7 and substantially midway between the inlet and outlet ends 8, 9 of the second tube 7. The second tube 7 has a radial hole 12 extending through the sidewall 10 and having a port 14 at the minimum cross-sectional area, the radial hole 12 receiving therein one end of an L-shaped support pipe 11, the other end of which is fitted in an axial hole 13 defined in a sidewall of the first tube 1. The hole 13 is held in fluid communication with a port 15 defined in the sidewall of the first tube 1 at the second cylindrical surface 6 adjacent to the junction between the conical taper surface 5 and the second cylindrical surface 6. The L-shaped pipe 11 and the hole 13 jointly constitute a flow passage 16 extending between the ports 14, 15 to provide fluid communication therethrough between the flow passage in the second tube 7 at the minimum cross-sectional area thereof and the flow passage in the first tube 1 at the outlet end 9 of the second tube 7. The second tube 7 is mounted in the first tube 1 by the support pipe 11 such that the outlet end 9 of the second tube 7 is located adjacent to the opening 15 in the sidewall of the first tube 1.

When a fluid flows smoothly through the flow passage in the first tube 1 along stream lines as illustrated in FIG. 1, a portion of the fluid also flows through the flow passage in the second tube 7, in which fluid flows at a greatest speed across the minimum cross-sectional area of the flow passage. As the fluid approaches the outlet end 9, the cross-sectional area of the flow passage progressively increases and hence the speed of flow of the fluid becomes progressively reduced. Accordingly, the following relationships result:

$$Pt < Po, \ Po \approx Po' \text{ and hence } Pt < Po' \qquad (1)$$

where Pt is the static pressure of the fluid at the minimum cross-sectional area of the flow passage in the second tube 7, Po is the static pressure of the fluid at the outlet end 9 of the second tube 7, and Po' is the static pressure of the fluid in the flow passage in the first tube 1 adjacent to the port 15 in the second cylindrical surface 6 of the first tube 1.

The difference between the pressures Pt and Po' causes a fluid flow to be produced through the passage 16 from the port 15 to the port 14 in the direction of the arrow A, as shown in FIG. 2. The fluid flow as it is ejected from the port 14 traverses the fluid flowing through the second tube 7, urging such fluid to be deflected and attached to the arcuate wall portion of the second tube 7 which is diametrically opposed to the port 14. As a result, there is developed a fluid flow B (including vortices) downstream of the port 14 as it is separated from the arcuate wall portion which is on the side of the port 14.

When the fluid flows through the flow passage in the first tube 1 along stream lines as shown in FIG. 2, the fluid flowing through the passage 16 into the second tube 7 at its minimum cross-sectional area and the separated flow B formed due to such flow cause the fluid pressures Pt, Po and Po' to satisfy the following relationship:

$$Pt \geq Po \ Po' \doteq \qquad (2)$$

At this time, the pressure difference which tends to force the fluid to flow through the passage 16 in the direction of the arrow A is eliminated, and hence the fluid fails to flow through the passage 16. Therefore, the fluid flow B also disappears, and the fluid starts to flow through the first tube 1 along the stream lines as shown in FIG. 1. Such a smooth fluid flow again causes the pressure differences as given by the expression (1), generating the fluid flows A and B. The fluid flow through the second tube 7 is repeatedly subjected alternately to fluid flow conditions as shown in FIGS. 1 and 2, whereupon the fluid pressures and/or static fluid pressures in the second tube 7 at its minimum cross-sectional area, adjacent to the outlet end 9, and in the fluid passage 16 are periodically changed.

When the first and second tubes 1, 7 and the flow passage 16 jointly produce such periodic variations of the flow conditions, or fluid vibrations, the rate of flow G of the fluid through the second tube 7 is linearly proportional to the frequency f of variations in the speed of flow or fluid pressure as can be understood from the principles of flow meters operable on the basis of fluid vibrations.

The present invention is directed to a flowmeter designed for determining the rate of flow G from the frequency f as detected of fluid vibrations.

As shown in FIG. 3, a flowmeter according to an embodiment of the present invention comprises a first double-walled tube 1 composed of inner and outer tubular members 101, 102 made of aluminum alloy by die casting, the inner tubular member 101 being concentrically fitted in the outer tubular member 102. The inner tubular member 101 comprises a first cylindrical surface 4, a conical taper surface 5 in the form of a truncated cone, and a second cylindrical surface 6 which is smaller in inside diameter than the first cylindrical surface 4. The surface 4, 5 and 6 are integrally joined and extend from an inlet end 2 to an outlet end 3 of the inner tubular member 101. A flow-rectifying device 23 of aluminum alloy is also mounted in the outer tubular member 102 and disposed at the inlet end 2 of the inner tubular member 101 in abutting relation to the end of the first cylindrical surface 4. The flow-rectifying device 23 comprises an annular member 21 fitted in the outer tubular member 102 and having an inside diameter equal to that of the first cylindrical surface 4, and a flow-rectifying grid 22 supported by the annular member 21. The inner and outer tubular members 101, 102 are assembled together by caps 103, 104 threaded on the ends of the outer tubular member 102. The caps 103, 104 have openings held in axial registry with openings defined by the first and second cylindrical surfaces 4, 6 to allow smooth flow of a fluid such as air through the first tube 1.

The conical taper surface 5 of the inner tubular member 101 has therein a recess 106 extending parallel to the central axis of the inner tubular member 101 and having a bottom 105 lying perpendicularly to the central axis of the inner tubular member 101. The inner tubular member 101 has a rectangular radial hole 107 defined in both the conical taper surface 5 and the second cylindrical surface 6 and located downstream of the recess 106 or closer than the recess 106 to the outlet end 3 in the axial direction. A hole 13 is also defined in the conical taper surface 5 and extends parallel to the axis of the inner tubular member 101 from the bottom 105 of the recess 106 to the hole 107 in communication therewith. An electrically insulating insert 111 molded of synthetic resin is fitted in the hole 107. The insert 111 has an inner surface 108 lying flush with the conical taper surface 5 and/or the second cylindrical surface 6, an outer peripheral surface 109 lying flush with the outer peripheral surface of the inner tubular member 101, and a passage 110 defined therethrough and having a port 15 opening at the surface 108 and communication with the hole 13 through the passage 110.

The flowmeter also comprises a second tube 7 which is of the construction identical to that of the second tube 7 as shown in FIG. 1, the second tube 7 being made of aluminum alloy by die casting. A support pipe 11 which is also formed of aluminum alloy has an attachment flange 17 shaped complementarily to the bottom 105 of the recess 106. The support pipe 11 includes an end having a port 14 fitted in a radial hole 12 in the second tube 7, and the other end inserted fittingly in the hole 13, with the attachment flange 17 being screwed to the bottom 107 of the recess 106. Thus, the second tube 7 is supported by the support pipe 7 within the first tube 1. The bore of the support pipe 11 and the passage 111 jointly define a flow passage 16 extending between the ports 14, 15.

A hot wire 30 connected to lead wires is suspended in the passage 10 in the insert 111, the lead wires being connected respectively to terminals 31, 31 partly embedded in the outer surface 109 of the insert 111 and projecting radially outwardly. The hot wire 30, the lead wires, and the terminals 31, 31 are assembled in the insert 111 when the latter is molded. The outer tubular member 102 has a radial aperture 112 in which the terminals 31, 31 are disposed. An electric socket 32 connected to an electric detecting circuit (described below) is snugly receivable in the aperture 112 for electrical connection to the terminals 31, 31. The electric socket 32 when inserted in the aperture 112 doubles as a stop for preventing relative rotation between the inner and outer tubular members 101, 102.

The electric detecting circuit comprises a rectifying filter and comparison pulse generator 33 for receiving an input signal from the terminals 31 through the socket 32, a pulse counter 34 for counting rectangular pulses delivered from the pulse generator 33, and a display unit 35 for directly indicating the count in the pulse counter 34 or displaying a rate of flow derived by such count through arithmetic operations, with a power supply (not shown) connected for energizing these circuit components.

The flowmeter thus constructed will operate as follows: A fluid such as air to be measured for its rate of flow is introduced through the inlet end 2 into the flow passage of the first tube 1 and discharged out of the outlet end 3, whereupon the fluid flow periodically undergoes alternate flow conditions as illustrated in FIGS. 1 and 2. Periodic variations in the speed of the fluid flowing through the passage 16 cause the hot wire 30 to supply the terminals 31 with an output signal having a frequency which is the same as the frequency of variations of the fluid flow in the passage 16, i.e., alternate generation and vanishing of the fluid flow in the passage 16. The comparison pulse generator 33 rectifies the output signal from the terminals 31 into a signal of a desired waveform and converts it into rectangular pulses, which are then counted by the counter 34, the count in which is displayed by the display unit 35 as either the frequency of the periodic variations of the fluid flow or the rate of flow as derived from such frequency through arithmetic operations.

Figure 4:
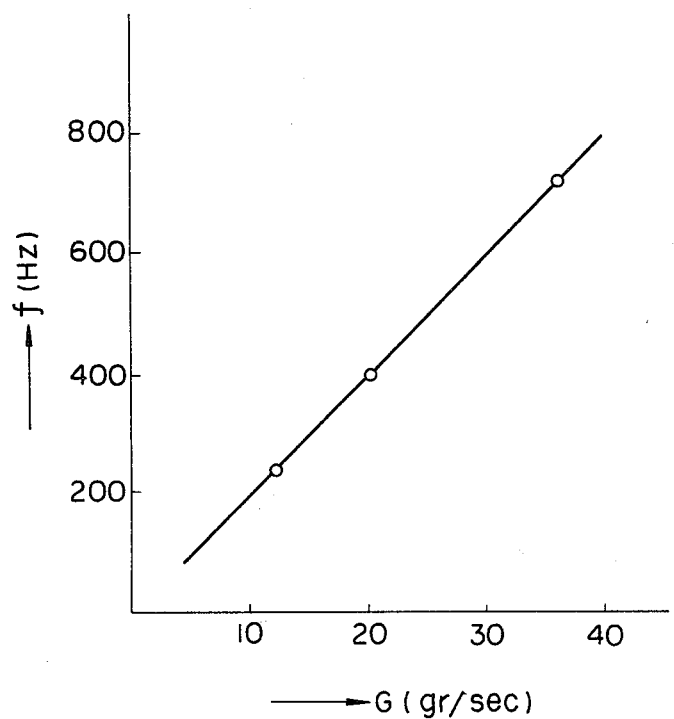
FIG. 4 is a graph showing rates of flow of air plotted against detected frequencies of vibrations of the air being measured.

A fluid with a known rate of flow was measured by the flowmeter of FIG. 3 to plot a relationship between its rate of flow G (gr/sec) and the frequency f (Hz) as detected by the hot-wire sensor of variations of the fluid flow. As illustrated in FIG. 4, it was confirmed that the rate of flow G is in linear relationship to the frequency f. For example, when the rate of flow G was 12 gr/sec, 20 gr/sec, and 36 gr/sec, the frequency f was 235 Hz, 400 Hz, and 710 Hz, respectively. These numerical examples indicate that the frequency f and the rate of flow G are linearly proportional to each other, and hence the rate of flow G can easily be derived and displayed by processing the frequency f through arithmetic operations.

In FIG. 3, a pressure sensor 40 or 41 may be provided in the insert 111 adjacent to the port 15 at the surface 108, or in the arcuate wall 10 of the second tube 7 adjacent to and upstream of the port 14, the pressure sensors 40, 41 having pressure-sensitive surfaces lying substantially flush with the wall surfaces. The pressure sensor 40 or 41 thus positioned can produce an output signal of a sine wave having the frequency f, which may be shaped into a suitable waveform by way half-wave rectification and converted into rectangular pulses by the comparison pulse generator. The pulses may then be counted by the pulse counter for the display of the rate of flow. As an alternate, the pressure sensors 40, 41 may be replaced with microphones used as sensors for flow rate measurement.

A grip handle 115 as shown by the two-dot-and-dash lines in FIG. 3 may be fixedly mounted on the outer tubular member 102 with the electric detecting circuit and the power supply housed in the grip handle 115, an arrangement which results in a portable hand-held flowmeter.

Figure 5:
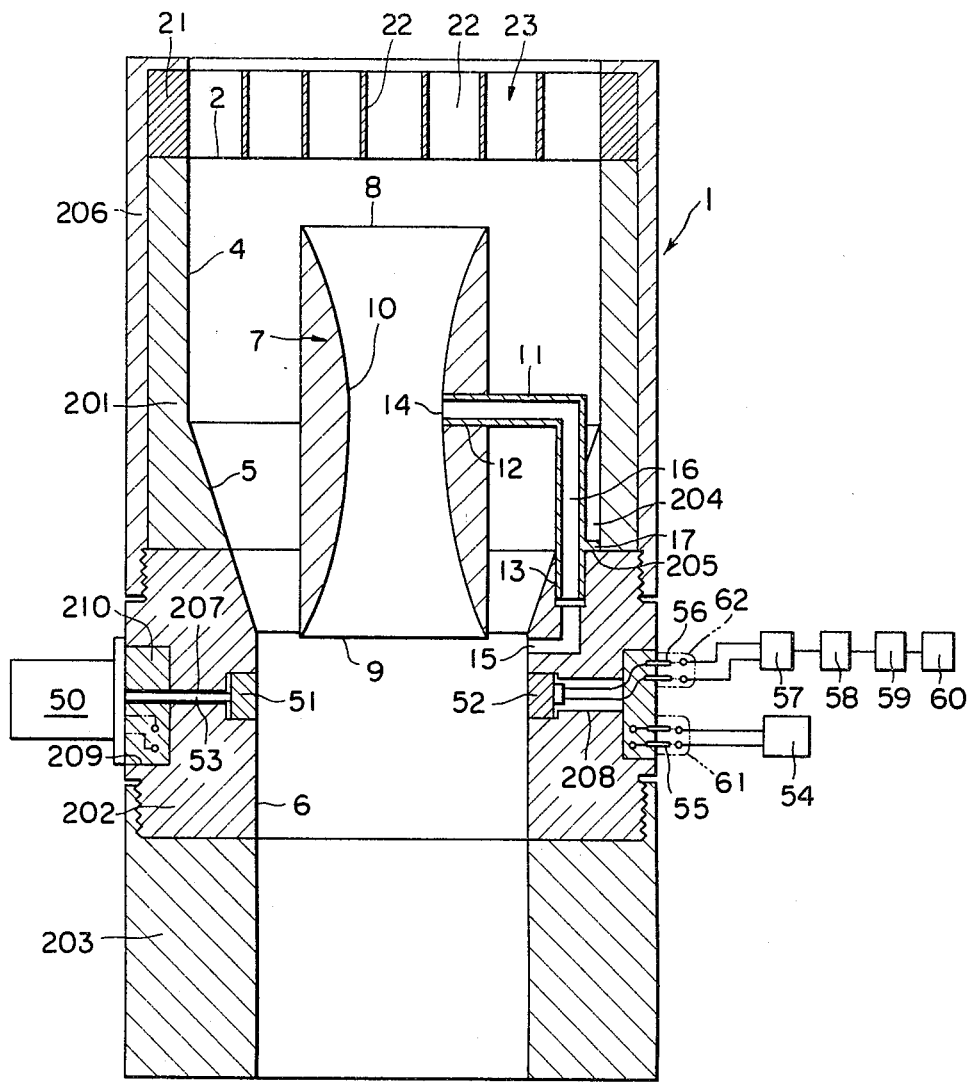
FIG. 5 is a cross-sectional view of a flowmeter according to another embodiment of the present invention.

According to a second embodiment as shown in FIG. 5, a flowmeter comprises a first tube 1 composed of three assembled cylindrical members 201, 202, 203 made of aluminum alloy by die casting. The cylindrical member 201 has a cylindrical surface 4 and substantially half of a conical taper surface 5, the other half thereof being defined by part of the cylindrical member 202. Thus, the cylindrical member 201 is separated from the cylindrical member 202 along a plane extending normal to the central axis of the first tube 1 substantially centrally of the conical taper surface 5. The cylindrical member 201 has in its part of the conical taper surface 5 a recess 204 extending parallel to the central axis of the first tube 1. The cylindrical members 202, 203 jointly define a cylindrical surface 6 and are held in threaded engagement with each other, the members 202, 203 being separated along a plane extending normal to the central axis of the first tube 1 substantially centrally of the cylindrical surface 6. The cylindrical member 202 has at its part of the conical taper surface 5 a hole defined in a surface 205 facing the recess 204 in the cylindrical member 201 and extending parallel to the central axis of the first tube 1 in communication with a port 15 opening radially into the flow passage in the first tube 1 at the cylindrical surface 6. A support pipe 11 of the same construction as that of the support pipe 11 shown in FIG. 3 has one end fitted in the hole 13 with a flange 17 thereof screwed to the surface 205 to fasten the support pipe 11 securely in position. A flow-rectifying device 23, similar in structure to the flow-rectifying device 23 illustrated in FIG. 3, is held in axial abutment with the cylindrical member 201 at its inlet end 2. A cap 206 is fitted over the flow-rectifying device 23 and the cylindrical member 201, and threaded on the cylindrical member 202.

The cylindrical member 202 has diametrically opposite stepped bores 207, 208 defined therethrough which receive therein a transmitter 51 and a receiver 52, respectively, of an ultrasonic transducer 50, the transmitter 51 and the receiver 52 being disposed downstream of and adjacent to the outlet end 9 of the second tube 7 and having their transmitting and receiving surfaces exposed to the flow passage in the first tube 1 and lying substantially flush with the cylindrical surface 6. The stepped bore 207 also receives therein a coupling rod 53 connected to the ultrasonic transmitter 51. The ultrasonic transmitter 51, the coupling rod 53, and the ultrasonic receiver 52 are acoustically insulated against sound transmission therebetween. The cylindrical member 202 also has an annular groove 209 formed in its outer circumferential surface and held in communication with the bores 207, 208. An insulative ring 210 of synthetic resin is disposed in the annular groove 209. Lead wires are embedded in the ring 210 which connect the ultrasonic transducer 50 to terminals 55 for an energization circuit 54 and also connect the ultrasonic receiver 52 to terminals 56, the terminals 55, 56 being partly embedded in the ring 210 projecting radially outwardly. The terminals 55 are electrically connected to the energization circuit 54 through a socket 61, and the terminals 56 are electrically connected to an electric detecting circuit (described below) through a socket 62.

The electric detecting circuit comprises a detector 57 for detecting an output signal generated by the ultrasonic receiver 52 and converting it into a signal of a sine wave, a pulse generator 58 for shaping the sine-wave signal into rectangular pulses by way of half-wave rectification, a pulse counter 59 for counting the rectangular pulses, and a display unit 60 for displaying the count in the pulse counter 59 as a frequency f or a rate of flow W as derived from the frequency f. The electric detecting circuit and the energization circuit 54 are connected to a power supply (not shown).

In operation, a fluid such as air flows into the flow passage in the first tube 1 through the flow-rectifying device 23 and the inlet end 2. While the fluid flows through the first tube 1, the fluid flow is periodically subjected to alternate fluid flow conditions as shown in FIGS. 1 and 2. More specifically, as illustrated in FIG. 2, a fluid flow occurs through the flow passage 15 in the direction of the arrow A, whereupon the fluid flow B is detached (to form vortices) from the arcuate wall 10 of the second tube 7 and flows away toward the outlet end 3 of the first tube 1. The frequency of an ultrasonic beam emitted from the transmitter 51 and received by the receiver 52 is modulated as vortices are generated upon detachment of fluid flows B from the arcuate wall 10. The output of the receiver 52 as it is thus modulated is detected by the detector 57 as a sine-wave signal, which is changed into a pulsed signal of a rectangular waveform by the pulse generator 58 through half-wave rectification. The pulses produced by the pulse generator 58 are counted by the pulse counter 59. The display unit 60 displays either the modulated frequency based on the count in the pulse counter 59, or the rate of flow derived from that frequency. Although not shown, the first tube 1 may be equipped with a grip handle similar to that shown in FIG. 3.

With the arrangements of the present invention, no physical quantities (absolute values) such as pressures or speeds of flow of a fluid are directly detected, but only the frequency of variations of such physical quantities is detected by a sensor, which is therefore not required to have high precision as to its output, but which needs a response good enough to detect the frequency of periodic changes of a physical quantity. Therefore, the sensor for use with the flowmeter of the present invention is relatively inexpensive to construct. The first tube 1, the second tube 7, and the flow passage 16 are so designed as to produce and sustain periodic oscillations of a fluid flow stably, and are relatively simple in structure. By appropriately selecting a cross-sectional ratio between the flow passages in the first and second tubes, the flowmeter can find usage in measuring a wide variety of rates of fluid flow. With fluid vibrations being caused by changing the static pressure of a fluid at the port 14 in the second tube 7 with a fluid flowing through the flow passage 16, variations in the fluid flow conditions may be regarded as either changes in the pressure of the fluid or changes in the speed of flow through the flow passage 16, so that various relatively simple and inexpensive sensors such for example as a pressure sensor or a speed sensor can also be utilized for use in the flowmeter of the invention. Furthermore, since the frequency of vibrations of a fluid is linearly proportional to the rate of flow of the fluid, an electrical circuit required to derive the rate of flow from the frequency through arithmetic operations is relatively simple in circuit arrangement.

Although specific embodiments of the invention have been illustrated and described, it will be understood that various alterations may be made therein without departing the scope of the invention as defined by the appended claims.

What is claimed is:

1. A flowmeter comprising:
   a first tube having an inlet and an outlet at axial ends thereof and a first flow passage having a cross-sectional area extending perpendicularly to a central axis of said first tube and smaller at said outlet than at said inlet, said first tube having a first port defined in a sidewall thereof and opening into said first flow passage;
   a second venturi-shaped tube disposed substantially concentrically within said first flow passage of said first tube and having an inlet and an outlet at axial ends thereof and a second flow passage having a cross-sectional area which is minimum substantially midway of said second tube in an axial direction thereof, said second tube having a second port defined in a sidewall thereof and opening into said second flow passage at the minimum cross-sectional area thereof;
   a third flow passage providing fluid communication between said first and second ports; and
   a sensor disposed in one of said third flow passage, said sidewall of the first tube and said sidewall of the second tube for detecting periodic variations in the condition of a fluid flowing through said first, second, or third flow passage, thereby detecting effectively the rate of flow of the fluid through said first and second tubes.

2. A flowmeter according to claim 1, said first tube comprising a first cylindrical surface connected to said inlet thereof, a second cylindrical surface connected to said outlet thereof and smaller in inside diameter than said first cylindrical surface, and a conical taper surface in the form of a truncated cone connected between said first and second cylindrical surfaces, said first, second, and conical taper surfaces jointly defining said first flow passage.

3. A flowmeter according to claim 2, wherein said outlet of said second tube is located adjacent to a position in which said conical taper surface and said second cylindrical surface are jointed to each other.

4. A flowmeter according to claim 1, wherein said first port is disposed adjacent to said outlet of said second tube.

5. A flowmeter according to claim 4, wherein said sensor comprises a pressure-sensitive sensor embedded in said sidewall of said first tube downstream of said first port, said pressure-sensitive sensor having a pressure-sensitive surface lying flush with said sidewall of said first tube.

6. A flowmeter according to claim 1, wherein said sensor comprises a pressure-sensitive sensor embedded in said sidewall of said second tube upstream of said second port, said pressure-sensitive sensor having a pressure-sensitive surface lying flush with said sidewall of said second tube.

7. A flowmeter according to claim 1, wherein said sensor comprises a thermoelectric sensor composed of a hot wire or a hot film located in said third flow passage.

8. A flowmeter according to claim 1, wherein said sensor comprises an acoustic sensor composed of an acoustic generator and an acoustic receiver disposed in diametrically opposite relation in said sidewall of said first tube downstream of said first port.

9. A flowmeter comprising:
   a first tube having an inlet and an outlet at axial ends thereof and a first flow passage having a cross-sectional area extending perpendicularly to a central axis of said first tube and smaller at said outlet than at said inlet, said first tube having a first port defined in a sidewall thereof and opening into said first flow passage;
   a second venturi-shaped tube disposed substantially concentrically within said first flow passage of said first tube and having an inlet and an outlet at axial ends thereof and a second flow passage having a cross-sectional area which is minimum substantially midway of said second tube in an axial direction thereof, said second tube having a second port defined in a sidewall thereof and opening into said second flow passage at the minimum cross-sectional area thereof;
   a third flow passage providing fluid communication between said first and second ports;
   a sensor disposed in one of said third flow passage, said sidewall of the first tube and said sidewall of the second tube for detecting periodic variations in the conditions of a fluid flowing through said first, second, or third flow passage; and
   an electric detecting circuit including a detector for detecting an output from said sensor, a counter for counting an output from said detector, and a display unit for displaying the rate of flow of the fluid as derived from the count in said counter.

* * * * *